United States Patent

Renner et al.

[11] Patent Number: 4,529,691
[45] Date of Patent: Jul. 16, 1985

[54] COLOR PHOTOGRAPHIC RECORDING MATERIAL CONTAINING COLOR COUPLERS

[75] Inventors: Günter Renner, Bergisch Gladbach; Erich Wolff, Solingen; Friedhelm Sommer, Leverkusen; Herbert Stark, Hagen; Dieter Stieler; Egon Meier, both of Leverkusen, all of Fed. Rep. of Germany

[73] Assignee: Agfa-Gevaert AG, Leverkusen, Fed. Rep. of Germany

[21] Appl. No.: 596,647

[22] Filed: Apr. 4, 1984

[30] Foreign Application Priority Data

Apr. 15, 1983 [DE] Fed. Rep. of Germany ....... 3313721

[51] Int. Cl.$^3$ .............................................. G03C 7/26
[52] U.S. Cl. .................. 430/556; 430/557; 430/558
[58] Field of Search .................. 430/556, 557, 558

[56] References Cited

U.S. PATENT DOCUMENTS 3,849,140 11/1974 Kuffner et al. ................ 430/556
4,133,958 1/1979 Boie et al. ..................... 430/556
4,289,847 9/1981 Ishikawa et al. ................ 430/557
4,352,873 10/1982 Toda et al. ..................... 430/556

Primary Examiner—J. Travis Brown
Attorney, Agent, or Firm—Connolly and Hutz

[57] ABSTRACT

Yellow couplers corresponding to the formula

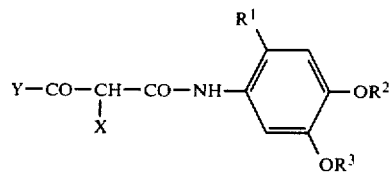

wherein

Y represents an aromatic, aliphatic or cycloaliphatic group,

X represents hydrogen or a releasable group, $R^1$ represents halogen, and $R^2$ and $R^3$ each represent an alkyl group having 1 to 20 carbon atoms, are readily soluble in oil formers and undergo coupling with a high color yield. They are resistant to heat and moisture and undergo color development to yield stable yellow dyes with an absorption maximum below 450 nm. They have a high absorption capacity in the near UV region and are virtually unaffected by fluctuations in the pH during processing.

1 Claim, 1 Drawing Figure

COLOR PHOTOGRAPHIC RECORDING MATERIAL CONTAINING COLOR COUPLERS

BACKGROUND OF THE INVENTION

This invention relates to a color photographic recording material having at least one silver halide emulsion layer and containing a non-diffusible α-acylacetanilide yellow coupler incorporated by emulsification, in which the anilide group is substituted with a halogen atom in the 2-position and with an alkoxy group at least in the 4-position and the 5-position.

It is known that color photographic images may be produced by chromogenic development, a process in which silver halide emulsion layers which have been exposed imagewise are developed with suitable color-forming developer substances, so-called color developers, in the presence of suitable color couplers. In this process, the oxidation product formed from the developer substances in correspondence with the silver image reacts with the color coupler to form a dye image. The color developers used are conventionally aromatic compounds containing primary amino groups, in particular those of the p-phenylenediamine series.

The color couplers and the dyes obtained from them by chromogenic development are required to satisfy numerous conditions. The color couplers should couple as rapidly as possible with the oxidation product of the color developer and should be able to yield as high a maximum color density as possible. Both the color couplers and the dyes obtained from them should be sufficiently stable to light, elevated temperature and moisture. This applies both to the fresh material and to the processed material. For example, residual color coupler still present in the image whites of the processed material should not undergo yellowing. The dyes should also be sufficiently resistant to gaseous reducing or oxidizing agents and they should be fixed in a diffusion-fast form in the image layer and should separate as a very fine grain during chromogenic development. Lastly, the dyes obtained from the color couplers as a result of chromogenic development should have a suitable absorption curve with a maximum corresponding to the color of the desired partial image and with as little side absorption as possible.

The requirements mentioned above apply particularly to yellow couplers because these are in many cases arranged in the uppermost color-producing layer of the color photographic recording material and are therefore not only more exposed to environmental influences but are also liable to influence the underlying layers, particularly in their sharpness. Any measures by which damage to the layers and particularly to the layer containing yellow coupler may be reduced are therefore advantageous.

BRIEF SUMMARY OF THE INVENTION

It is an object of the present invention to provide yellow couplers for a color photographic recording material which are readily soluble in various oil formers and which, when dissolved in a very small quantity of oil former, will be able to undergo coupling with a very high color yield to form yellow dyes having an absorption maximum below 450 nm. Both the couplers and the dyes should remain stable under the influence of heat, moisture and light. The couplers should have a high absorption capacity in the near UV region and their coupling activity should be virtually unaffected by any changes in pH.

DETAILED DESCRIPTION

Figure 1:
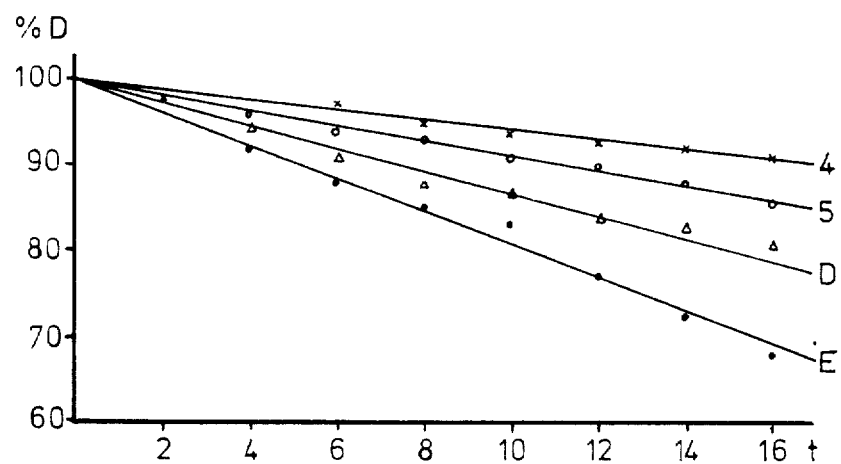
FIG. 1 is a graph representing stability tests with density shown on the ordinate and time along the abscissa.

The present invention provides a color photographic recording material having at least one light-sensitive silver halide emulsion layer and a non-diffusible yellow coupler associated with this layer, characterised in that the yellow coupler corresponds to the following formula:

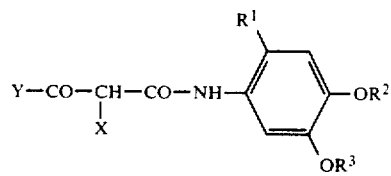

wherein

Y represents an optionally substituted aromatic group or an aliphatic or cycloaliphatic group, X represents a hydrogen atom or a group which may be released by color coupling, $R^1$ represents a halogen atom, e.g. fluorine, chlorine or bromine, and $R^2$ and $R^3$ represent identical or different alkyl groups each having 1 to 20 carbon atoms, including substituted alkyl groups, e.g. benzyl.

The yellow couplers according to the invention are also equipped with ballast groups which enable them to be incorporated in a diffusion-fast form in the hydrophilic colloids conventionally used in photographic recording materials. These groups are preferably organic groups, generally containing straight-chained or branched aliphatic groups and optionally also containing carbocyclic or heterocyclic aromatic groups generally having from 8 to 20 carbon atoms. These ballast groups are attached to the remainder of the molecule either directly or indirectly, e.g. through one of the following groups: —NHCO—, —NHSO$_2$—, —NR— (wherein R represents hydrogen or alkyl), —O— or —S—. Since the diffusion characteristics depend upon the molecular size of the whole compound, it is in some case sufficient to use only short-chained groups as ballast groups, e.g. if the molecule as a whole is large enough.

The aromatic group represented by Y may be in particular a phenyl group carrying one or more substituents such as, for example, halogen atoms, alkoxy groups or acylamino groups. Such a phenyl group may also be substituted in one or two positions with other yellow coupler structures corresponding to the formula:

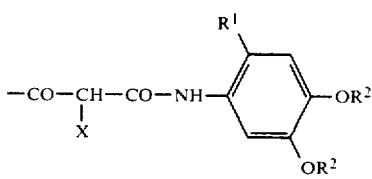

wherein X, R¹, R² and R³ have the meaning already indicated.

An aliphatic group represented by Y is preferably a tertiary alkyl group, in particular tertiary butyl. A cycloaliphatic group represented by Y may be, for example, a cyclohexyl, norbornyl or adamantyl group.

If X represents a group which may be released during color coupling, it is preferably a cyclic group attached through an oxygen atom or a nitrogen atom, in particular through a ring nitrogen atom, e.g. an optionally substituted 5-membered or 6-membered heterocyclic ring attached through a ring nitrogen atom. Such releasable groups normally confer on the coupler the behaviour of a 2-equivalent coupler, i.e. the coupler requires only half as much developable silver halide for color coupling as the corresponding 4-equivalent coupler in which X is a hydrogen atom. Examples of suitable releasable groups are shown below.

Releasable groups

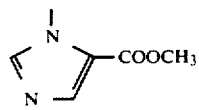 (1)

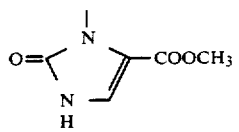 (2)

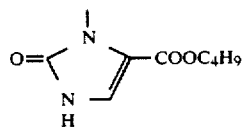 (3)

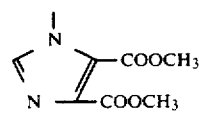 (4)

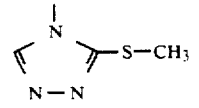 (5)

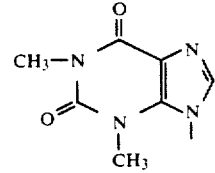 (6)

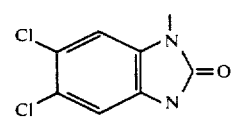 (7)

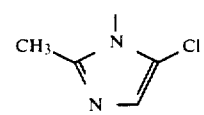 (8)

-continued
Releasable groups

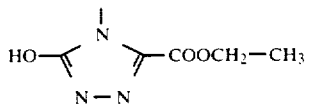 (9)

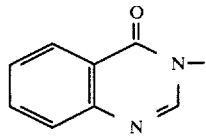 (10)

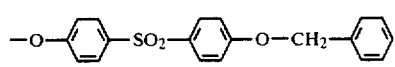 (11)

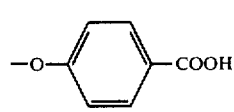 (12)

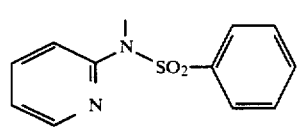 (13)

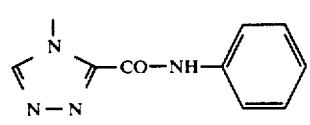 (14)

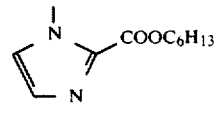 (15)

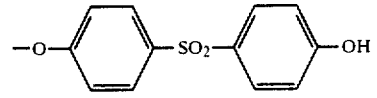 (16)

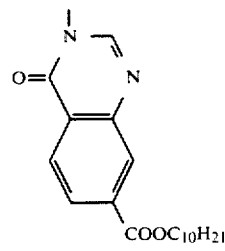 (17)

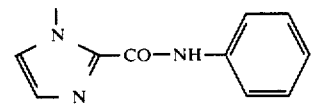 (18)

Examples of yellow couplers according to the invention are listed below. The number entered in column X denotes the releasable group from the numbered list given above.

| Coupler | Y | X | R¹ | R², R³ |
|---|---|---|---|---|
| 1 | 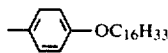 —⟨⟩—OC₁₆H₃₃ | 11 | Cl | —CH₃ |
| 2 | " | 9 | Cl | —CH₃ |
| 3 | " | 7 | Cl | —CH₃ |
| 4 | " | 2 | Cl | —CH₃ |
| 5 | " | 6 | Cl | —CH₃ |
| 6 | " | 18 | Cl | —CH₃ |
| 7 | " | 3 | Cl | —CH₃ |
| 8 | " | 5 | Cl | —CH₃ |
| 9 | " | 12 | Cl | —CH₃ |
| 10 | " | 13 | Cl | —CH₃ |
| 11 | " | 10 | Cl | —CH₃ |
| 12 | " | 5 | Br | —CH₃ |
| 13 | " | 4 | Br | —CH₃ |
| 14 | " | 1 | Br | —CH₃ |
| 15 | " | 1 | F | —CH₃ |
| 16 | " | 6 | Cl | —CH(CH₃)₂ |
| 17 | " | 2 | Cl | —CH(CH₃)₂ |
| 18 | " | 11 | Cl | —CH(CH₃)₂ |
| 19 | " | 11 | Br | —CH(CH₃)₂ |
| 20 | " | 10 | Br | —CH(CH₃)₂ |
| 21 | " | 14 | Cl | —CH(CH₃)₂ |
| 22 | 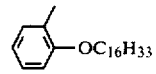 ⟨⟩—OC₁₆H₃₃ | 7 | Cl | —CH₃ |
| 23 | " | 6 | Cl | —CH₃ |
| 24 | " | 8 | Cl | —CH₃ |
| 25 | " | 5 | Cl | —CH₃ |
| 26 | " | 2 | Cl | —CH₃ |
| 27 | 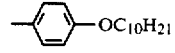 —⟨⟩—OC₁₀H₂₁ | 7 | Cl | —CH₂—⟨⟩ |
| 28 | " | 11 | Cl | " |
| 29 | " | 1 | Cl | " |
| 30 | " | 2 | Br | " |
| 31 |  CH₃O—⟨⟩— | 6 | Cl | —C₈H₁₇ |
| 32 | " | 15 | Cl | —C₈H₁₇ |
| 33 | " | 1 | Cl | —C₈H₁₇ |
| 34 | " | 11 | Cl | —C₈H₁₇ |
| 35 | " | 2 | Cl | —C₈H₁₇ |
| 36 | 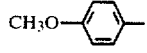 CH₃O—⟨⟩—OCH₃ | 1 | Cl | —C₈H₁₇ |
| 37 | " | 6 | Cl | —C₈H₁₇ |
| 38 | " | 12 | Cl | —C₈H₁₇ |
| 39 | " | 3 | Cl | —C₈H₁₇ |
| 40 | 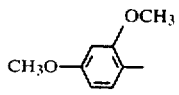 (CH₃)₂CH—O—⟨⟩— | 2 | Cl | —C₆H₁₃ |
| 41 | " | 7 | Cl | —C₆H₁₃ |
| 42 | " | 9 | Cl | —C₆H₁₃ |
| 43 | 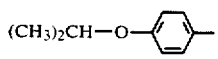 Cl—⟨⟩— | 6 | Cl | —C₈H₁₇ |
| 44 | " | 11 | Cl | —C₈H₁₇ |
| 45 | 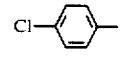 C₁₆H₃₃—SO₂—NH—⟨⟩— | 7 | Cl | —CH₃ |
| 46 | " | 1 | Cl | —CH₃ |
| 47 | " | 16 | Cl | —CH₃ |

-continued

| Coupler | Y | X | R$^1$ | R$^2$, R$^3$ |
| --- | --- | --- | --- | --- |
| 48 | (3-phenyl)-NH-CO-CH(C$_2$H$_5$)-O-(2,4-di-t-C$_5$H$_{11}$-phenyl) | 1 | Cl | —C$_2$H$_5$ |
| 49 | " | 11 | Cl | —C$_2$H$_5$ |
| 50 | " | 10 | Cl | —C$_2$H$_5$ |
| 51 | " | 6 | Br | —CH$_3$ |
| 52 | " | 15 | Br | —CH$_3$ |
| 53 | " | 12 | Br | —CH$_3$ |
| 54 | —t-C$_4$H$_9$ | 11 | Cl | —C$_8$H$_{17}$ |
| 55 | —t-C$_4$H$_9$ | 15 | Cl | —C$_8$H$_{17}$ |
| 56 | —t-C$_4$H$_9$ | 16 | Cl | —C$_8$H$_{17}$ |
| 57 | —t-C$_4$H$_9$ | 7 | Cl | —C$_8$H$_{17}$ |
| 58 | —t-C$_4$H$_9$ | 17 | Cl | —CH$_3$ |

Coupler 59

C$_{16}$H$_{33}$O—(phenyl)—CO—CH($_6$)—CO—NH—(4-Cl, 2-OCH$_3$, 5-OC$_{16}$H$_{33}$-phenyl)

Coupler 60

(5-Cl, 2-CH$_3$O, 4-CH$_3$O-phenyl)—HN—CO—CH($_6$)—C(=O)—(2-CH$_3$O, 5-OCH$_3$-phenylene)—C(=O)—CH($_6$)—CO—NH—(5-Cl, 2-OCH$_3$, 4-OCH$_3$-phenyl)

The yellow couplers according to the invention are synthesized by methods known in the literature. Alkylation of pyrocatechol and halogenation of the resulting diether followed by nitration and reduction of the multiply substituted nitrobenzene yields the substituted aniline, which is then condensed with the β-ketoester under the usual reaction conditions. The group released during color coupling (releasable group) is introduced into the molecule by suitable oxidation of the 4-equivalent coupler, again by known reaction steps. Synthesis of the compounds according to the invention is illustrated in the examples (preparative) given below:

Coupler 1

1.1: 4-Chloropyrocatechol dimethylether:

34.5 g (0.25 mol) of pyrocatechol dimethylether are dissolved in 50 ml of glacial acetic acid. A solution of 33.8 g (0.25 mol) of sulfuryl chloride is added within 90 minutes of 0° C. and the reaction mixture is stirred for 30 minutes and precipitated in water. Yield: 37 g=85.7%.

1.2: 4-Chloro-5-nitro-1,2-dimethoxybenzene:

349.5 g of Compound 1.1 are slowly added dropwise to 220 ml of 65% nitric acid and 300 ml of water at a temperature not rising above 70° C. The reaction mixture is then stirred for 2 hours at 65° C. and cooled and the precipitated reaction product is separated by suction filtration. Yield: 392 g=90% of theoretical yield, pale yellow crystals, m.p. 106°–108° C.

1.3: 2-Chloro-4,5-dimethoxyaniline:

100 g of product 1.2 are hydrogenated in 1000 ml of ethanol at 10 bar hydrogen pressure and 50° C. within 4 hours, using Raney nickel as catalyst. The Raney nickel is then separated by suction filtration and the amine is precipitated with aqueous hydrochloric acid. The hydrochloric acid salt is suction-filtered, again stirred up in water, and neutralized with NaOH. The free amine now precipitated is suction-filtered. Yield: 66 g=77% of theoretical yield, pale grey powder.

1.4 α-(4-cetyloxybenzoyl)-2-chloro-4,5-dimethoxyacetanilide:

375.4 g (2.0 mol) of product 1.3, 920 g (2.2 mol) of p-cetyloxybenzoyl acetic ester and 1300 ml of xylene are heated to boiling. 1100 ml of xylene are distilled off and the solution is stirred into 5000 ml of butanol. After cooling, the product is suction-filtered and the filter residue is repeatedly washed with cold methanol. Yield: 920 g=80% of theoretical yield, white crystals, m.p. 120° C.

1.5 α-Chloro-α-(4-cetyloxybenzoyl)-2'-chloro-4',5'-dimethoxyacetanilide:

574 g (1.0 mol) of product 1.4 are dissolved in 1700 ml of methylene chloride and chlorinated with 140 g (1.04 mol) of sulfuryl chloride at room temperature. The methylene chloride is distilled off under vacuum and the residue is used for the reaction described below with further purification.

1.6 α-[4-(4'-benzyloxybenzoylsulfonyl)-phenoxy]-(4"-cetyloxybenzoyl)-2'''-chloro-4''',5'''-dimethoxyacetanilide:

25 g (0.041 mol) of product 1.5 were dissolved in 125 ml of dimethylformamide together with 16.8 g (0.049 mol) of 4-(4'-benzyloxyphenylsulfonyl)-phenol. 5.4 g of sodium methylate dissolved in 18 ml of methanol were added dropwise at 50°-60° C. Stirring was continued for a further 30 minutes at 50° C. and the reaction mixture was then stirred into ice water and 50 ml of concentrated hydrochloric acid. The product was suction-filtered, washed and dried. Yield: 38 g of crude product, which was recrystallized from acetonitrile to yield 25 g=67% of theoretical yield, white crystals, melting point 112°-114° C.

Coupler 2

25 g of product 1.4 are chlorinated as described under 1.5. The residue is dissolved in 300 ml of acetonitrile and added dropwise to a mixture of 7.1 g of 3-carbethoxy-5-hydroxy-1,2,4-triazole and 20 ml of diazabicycloundecene at 50° C. The reaction mixture is stirred for one hour and precipitated in aqueous acid solution. The organic phase is separated and concentrated by evaporation. The residue is recrystallised from ethanol. 26.5 g=62% of theoretical yield of Coupler 2 are obtained. White crystals, m.p. 107°-139° C.

Coupler 3

22 g of product 1.5 and 11 g of 5,6-dichloro-2-ethyl-benzimidazolone are dissolved in 180 ml of dimethylacetamide. 15 ml of tetramethylguanidine are added dropwise at 50° C. The reaction mixture is then stirred into 1800 ml of normal hydrochloric acid at 5° C. for one hour and the oil which precipitates is taken up in ethyl acetate. The organic phase is washed, dried and concentrated by evaporation. The residue is purified by column chromatography, using a mixture of cyclohexane and ethyl acetate as elutant. Yield: 15 g=52% of theoretical yield, m.p. 109°-110° C.

Couplers 4 to 11 are synthesized by the same method as described for Coupler 1.

Coupler 12

12.1: 4-Bromopyrocatechol dimethyl ether:

69 g (0.5 mol) of dimethoxybenzene are dissolved in 200 ml of methylene chloride. 80 g (0.5 mol) of bromine are added dropwise at 0° C. Stirring is then continued for one hour at the same temperature, the organic phase is washed with water, and the solvent is distilled off. Yield determined by gas chromatography: 89.5%.

Compound 12.1 is reacted as described under the headings 1.2 to 1.5.
12.6:

19.6 g (0.03 mol) of compound 12.5 are dissolved in 150 ml of hexamethylphosphoric acid triamide. 4.6 g (0.04 mol) of 3-methylthio-1,2,4-triazole are added. 10 ml of triethylamine are added dropwise to the resulting solution within 2 hours at 30° C. Stirring is continued for a further 30 minutes and the product is then precipitated in 1000 ml of normal hydrochloric acid. The residue is taken up in ethyl acetate, repeatedly washed with water, dried and evaporated. Recrystallization from ethanol yields white crystals, m.p. 85°-89° C., yield 12.2 g 61% of theoretical yield.

The starting compound 15.1 was obtained by diazotization of 4-aminopyrocatechol dimethylether in the presence of hydrofluoboric acid and decomposition of the diazonium tetrafluoroborate with copper-I-chloride at 60°-80° C.

Coupler 15 was obtained by reactions analogous to those described above.

1,2-Diisopropyloxybenzene was used as starting compound for Couplers 16 to 21.

Couplers 22 to 25 were obtained using o-cetyloxybenzoylacetic ester.

The higher anilinoethers (see Couplers 31 to 44 and 54 to 57) were obtained in high yields by the alkylation of pyrocatechol with the corresponding alkyl bromides. The following method of synthesis was found advantageous for Coupler 33:

29 g (0.05 mol) of the 4-equivalent coupler and 7.6 g of the imidazole carboxylic acid methyl ester were dissolved in 150 ml of acetone. A solution of 10 g of bromine in 50 ml of acetonitrile was slowly added dropwise at room temperature. The product was precipitated with water, taken up in ethanol, washed, separated off, dried and concentrated by evaporation. The residue could be recrystallized from ethanol. Yield: 23 g=66% of theoretical yield of a white, crystalline substance, m.p. 125°-127° C.

Coupler 59 was obtained by chlorination of 2-methoxyphenol and alkylation of the resulting compound with cetyl bromide and the reaction steps otherwise analogous to those already described.

The yellow couplers according to the invention containing the 2-halogen-4,5-dialkoxyanilide group have sufficiently hydrophilic characteristics, obviously due to the presence of the adjacent alkoxy groups (the anilide group may contain further, additional alkoxy groups) to enable dyes having the required sensitivity and maximum color density to be developed from them without the aid of special developer additives such as benzyl alcohol, for example, to act as mediators between the hydrophilic and the hydrophobic phase. This action of the hydrophilic centres (ether bonds) also has a positive effect on the "competing reaction ratio" of color couplers described in DE-A 2 456 076.

The term "competing reaction ratio" refers to the ratio of the relative reactivities of a yellow coupler in the presence and absence, respectively, of a competing coupler such as citrazinic acid, H-acid or white coupler, as expressed by the equation:

$$CRR = \frac{D_o}{D_I}$$

where $D_0$=maximum color density of a photographic layer which has been developed in a color developer without a competing coupler, and $D_1$=maximum color density of the same layer developed in a color developer containing a competing coupler.

The positive influence described above of the yellow couplers according to the invention in photographic layers manifests itself in a lower competing reaction ratio. Compared with known yellow couplers, the novel yellow couplers according to this invention have the advantage that, in the process of color coupling, they are not influenced to such an extent by the presence of competing couplers. This manifests itself in a lower competing reaction ratio and higher color yields in a given development process. The advantages of a higher color yield, such as the smaller quantity of coupler and silver required, especially in the yellow layer, are well known and need not be further described here.

The yellow couplers according to the invention are also distinguished above all by their excellent solubility and low tendency to crystallization in organic solvents, especially in solvents with high boiling points which are immiscible with water, e.g. isomeric mixtures of tricresyl phosphate, or dibutyl phthalate.

This also has the advantageous effect of reducing the quantity required to be applied in each layer.

Furthermore, the yellow couplers according to this invention have excellent resistance to diffusion in photographic layers, both during the casting process and during photographic processing.

Another advantage of the yellow couplers according to the invention is their high resistance to moisture and heat as well as the resistance of the yellow dyes produced from them to heat, moisture and incident light.

The yellow couplers give rise to yellow dyes which have the desired absorption maximum below 450 nm. The couplers themselves have a high adsorption capacity in the near UV region, which is advantageous for the stability of the image dyes produced in the lower lying layers.

Lastly, the yellow couplers according to the present invention are comparatively unaffected by fluctuations in pH during processing, especially during development.

The combination of excellent solubility in organic solvents and excellent diffusion resistance on the one hand with compatibility with water on the other hand is a particularly unexpected, unforeseeable property of the couplers according to this invention.

During preparation of the light-sensitive photographic recording material, the diffusion-resistant yellow couplers according to the present invention may be incorporated in known manner in the casting solution of the silver halide emulsion layers or other colloidal layers. For example, the oil-soluble or hydrophobic yellow couplers preferably may be added to a hydrophilic colloid solution from a solution in a suitable coupler solvent (oil former) optionally in the presence of a wetting agent or dispersing agent. The hydrophilic casting solution may, of course, contain the conventional additives in addition to the binder. The solution of color coupler need not be directly dispersed in the casting solution for the silver halide emulsion layer or any other water-permeable layer but may advantageously first be dispersed or dissolved in an aqueous, light-insensitive solution of a hydrophilic colloid, and the resulting mixture may then be mixed with the casting solution for the light-sensitive silver halide emulsion layer or some other water-permeable layer, optionally after removal of the organic solvent used, before it is applied.

The light-sensitive silver halide emulsions used may be emulsions of silver chloride, silver bromide or mixtures thereof, optionally containing a small quantity of silver iodide of up to 10 mol-%, in one of the commonly used hydrophilic binders. The binder used for the photographic layers is preferably gelatine but this may be partly or completely replaced by other natural or synthetic binders.

The emulsions may be chemically or spectrally sensitized in the usual manner, and the emulsion layers as well as other light-insensitive layers may be hardened with known hardeners in the usual manner.

To produce color photographic images, the color photographic recording material according to the invention, containing the new yellow coupler in at least one silver halide emulsion layer, is developed with a color developer compound. Any developer compounds whose oxidation products are capable of reacting with color couplers to form azomethine dyes may be used as color developer compounds. These include aromatic compounds of the p-phenylenediamine series containing at least one primary amino group, for example N,N-dialkyl-p-phenylenediamines such as N,N-diethyl-p-phenylenediamine, 1-(N-ethyl-N-methylsulfonamidoethyl)-3-methyl-p-phenylenediamine, 1-(N-ethyl-N-hydroxyethyl)-3-methyl-p-phenylenediamine and 1-(N-ethyl-N-methoxyethyl)-3-methyl-p-phenylenediamine.

EXAMPLE 1

Color photographic recording materials 1 to 6 were prepared by applying the following layers in the sequence given on to a transparent layer support of cellulose triacetate. The quantities indicated are based in each case on 1 m². The quantity of silver halide applied is indicated in terms of the corresponding quantity of AgNO$_3$.

Layer 1: Silver iodobromide emulsion (6 mol-% iodide) containing 2.5 g of AgNO$_3$, 2.5 g of gelatine and 2.5 mmol of one of the yellow couplers entered in Table 1 below. The yellow couplers were dispersed in the emulsion with the aid of an equal quantity by weight of dibutyl phthalate, i.e. as 1:1 mixture.

Layer 2: 1.5 g of gelatine and 0.7 g of a hardener corresponding to the following formula

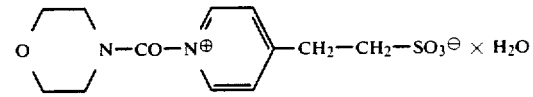

A sample strip of each of the recording materials 1 to 6 was exposed behind a step wedge and subjected at 38° C. to a reversal processing as described in the British Journal of Photography, 1981, pages 889 et seq and using the following color developer (F 1):

| | |
|---|---|
| Nitrilotriacetic acid | 2 g |
| Trisodium phosphate sicc. | 20 g |
| Potassium bromide sicc. | 1 g |
| Potassium iodide, 0.1% solution | 20 g |
| Sodium sulfite sicc. | 4.5 g |
| 2,2'-Ethylene-dithiodiethanol | 1 g |
| 4-(N—ethyl-N—methyl-sulfonamido-ethyl)-2-methyl-phenylenediamine sesquisulfate monohydrate | 11 g |
| Citrazinic acid | 1.3 g |
| made up with water to 1000 ml, pH | 11.6. |

The values obtained (maximum color density Dmax, specific sensitivity E$_{sp}$ and graininess $\sigma_D \cdot 10^{-2}$) are shown in Table 1 below. The specific sensitivity E$_{sp}$ is determined at the density given by the expression $$D = \frac{1}{2}(D\max + D\min)$$

and is expressed in relative log I.t values.

The graininess is measured as described in T. H. James in The Theory of the Photographic Process, 4th Edition (1977), pages 618–621.

TABLE 1

| Material | Coupler | Dmax | $E_{sp}$ | $\sigma_D \cdot 10^2$ |
|---|---|---|---|---|
| 1 | A | 2.45 | 22.5 | 4.3 |
| 2 | B | 2.68 | 21.1 | 5.7 |
| 3 | 4 | 2.91 | 21.7 | 4.6 |
| 4 | 5 | 3.15 | 21.3 | 4.1 |
| 5 | 16 | 3.38 | 21.3 | 5.0 |
| 6 | 31 | 3.35 | 21.3 | 4.8 |

For the same quantity of silver applied, the color couplers according to the invention yield higher maximum color densities than the Comparison Couplers A and B and the color graininess is even improved compared with those of the Comparison Couplers.

Comparison Coupler A

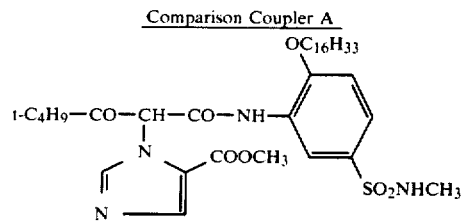

(Coupler 11 from US-A-4 049 458)

Comparison Coupler B

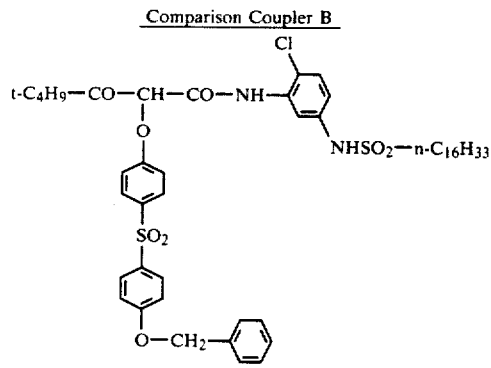

(Coupler 12 of DE-A-2 456 076)

EXAMPLE 2

A further sample strip of each of the recording materials described in Example 1 was exposed behind a step wedge and subjected to a negative development process as described in the British Journal of Photography, 1974, page 597 et seq. The results are entered in Table 2 below.

TABLE 2

| Material | Coupler | Dmax | Dmin | Fog % | $E_{sp}$ |
|---|---|---|---|---|---|
| 1 | A | 3.15 | 0.76 | 24 | 28.3 |
| 2 | B | 3.25 | 0.62 | 19 | 25.9 |
| 3 | 4 | 4.23 | 0.60 | 14 | 26.9 |
| 4 | 5 | 4.43 | 0.58 | 13 | 26.9 |
| 5 | 16 | 4.28 | 0.43 | 10 | 28.6 |
| 6 | 31 | 4.67 | 0.33 | 7 | 28.2 |

The value in column 5 is the Dmin/Dmax ratio given in percent.

The yellow couplers according to the invention not only provide a higher maximum color density and therefore a higher color yield but also a lower fog. This is expressed particularly clearly in the "fog %" value. The higher color yield provides the possibility of altering the AgNO₃/coupler ratio in favour of improved graininess by reducing the quantity of silver application. At the same time, the sharpness is improved in the green- and red-sensitive layers arranged underneath the blue-sensitive layer containing the yellow coupler.

EXAMPLE 3

A sample strip from each of the recording materials 1 to 6 described in Example 1 was exposed behind a step wedge and processed as in Example 1, but the color developer bath was adjusted with KOH or phosphoric acid to one of the pH values, 11.0; 11.3; 11.6 and 11.9.

The maximum color densities of the developed sample strips are shown in Table 3.

TABLE 3

| | | Dmax at pH | | | |
|---|---|---|---|---|---|
| Material | Coupler | 11.0 | 11.3 | 11.6 | 11.9 |
| 1 | A | 2.43 | 2.45 | 2.45 | 2.35 |
| 2 | B | 2.02 | 2.40 | 2.68 | 2.93 |
| 3 | 4 | 2.81 | 2.93 | 2.91 | 2.88 |
| 4 | 5 | 3.00 | 3.06 | 3.15 | 3.07 |
| 5 | 16 | 3.26 | 3.37 | 3.38 | 3.25 |
| 6 | 31 | 3.32 | 3.34 | 3.35 | 3.17 |

The maximum color densities of the yellow couplers according to the invention are not only higher than those of Comparison Couplers A and B but are also substantially constant over a relatively wide pH range. The photographic image-producing characteristics of the yellow couplers according to the invention are therefore to a large extent unaffected by fluctuations in pH in the color developer.

EXAMPLE 4

Color photographic recording materials 7 to 11 were prepared as in Example 1 but using the following layer 1:

Layer 1: Silver iodobromide emulsion (3.8 mol-% iodide) containing 1.0 g of AgNO₃, 1.5 g of gelatine and 1.0 mmol of a yellow coupler, 5, 16, 31, A and B.

Two sample strips of each of the recording materials prepared as described above were exposed behind a step wedge and subjected to reversal processing as in Example 1 but with different colour developer baths. One of the two samples was in each case developed in a color developer (F 2) having the following composition:

| | |
|---|---|
| Nitrilotriacetic acid | 2 g |
| Trisodium phosphate sicc. | 20 g |
| Potassium bromide | 1 g |
| Potassium iodide, 0.1% | 20 ml |
| Sodium sulfite | 4.5 g |
| 3,6-Dithiaoctane-1,8-diol | 1 g |
| N—Ethyl-N—hydroxyethyl-3-methyl p-phenylene-diaminesulfate monohydrate | 8 g |
| made up with water to 1000 ml. | |

The second strip was developed in a color developer (F 3) having the same composition as color developer (F 2) but in addition containing 1.3 g of citrazinic acid as a competing coupler. Both color developers were adjusted to pH 11.6 with KOH or phosphoric acid.

For each of the yellow couplers investigated, Table 4 below shows the Dmax values obtained after development in both color developers and the CRR value, which was determined from the following equation:

$$CRR = \frac{Dmax\ (F\ 2)}{Dmax\ (F\ 3)}$$

CRR is the "competing reaction ratio" expressed as the quotient of the maximum color density obtained in the absence of a competing coupler and the maximum color density obtained in the presence of a competing coupler. The method of determining the CRR value is described in DE-A No. 2 456 076.

TABLE 4

| Material | Coupler | Dmax (F 2) | Dmax (F 3) | CRR |
|---|---|---|---|---|
| 7 | A | 1.47 | 1.37 | 1.07 |
| 8 | B | 1.38 | 1.31 | 1.05 |
| 9 | 5 | 1.62 | 1.61 | 1.01 |
| 10 | 16 | 1.46 | 1.45 | 1.00 |
| 11 | 31 | 1.45 | 1.44 | 1.00 |

The yellow couplers according to the invention almost attain the theoretically limiting CRR values of 1.00.

EXAMPLE 5

Color photographic recording materials 12 to 15 were prepared as in Example 1 but using the following layer 1:

Layer 1: Silver iodobromide emulsion (4.2 mol-% iodide) ripened with gold and sulfur and containing, for 40.8 g of $AgNO_3$, 30.6 g of gelatine, 480 mg of 4-hydroxy-6-methyl-1,3,3a,7-tetraazaindene, 20 mg of a sensitizer corresponding to the following formula:

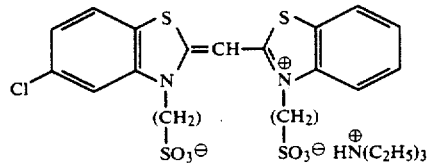

24 mg of 3-mercapto-5-(2-furyl)-1,2,4-triazole (stabilizer according to DE-A No. 2 711 942) and $39.2 \cdot 10^{-3}$ mol of one of the four yellow couplers indicated in Table 5 below.

The four different emulsion samples were applied to a layer support in such quantities that, when processed according to the British Journal of Photography, 1981, pages 889 et seq, comparable maximum color densities were obtained. The quantities of silver application required (g $AgNO_3/m^2$) were determined by preliminary experiments.

One sample strip of each of the recording materials was stored for 14 days at 57° C. and 35% relative humidity before exposure. For comparison, another sample strip of each of the recording materials was stored at 10° C. for the same length of time. The sample strips were then exposed behind a step wedge and subjected to the reversal process described. The quantities of silver application and the maximum colour densities of sample strips which had been stroed under controlled conditions of elevated temperature and moisture, measured as a percentage of the maximum colour density of sample strips stored at the lower temperature, are shown in Table 5 below.

TABLE 5

| Material | Coupler | g $AgNO_3/m^2$ | relative Dmax (%) |
|---|---|---|---|
| 12 | A | 3.3 | 45 |
| 13 | C | 3.6 | 73 |
| 14 | 4 | 2.3 | 80 |

TABLE 5-continued

| Material | Coupler | g $AgNO_3/m^2$ | relative Dmax (%) |
|---|---|---|---|
| 15 | 5 | 2.1 | 87 |

The yellow couplers according to the invention are clearly superior to the comparison couplers, both as regards their stability in storage and in their much lower silver halide requirement for obtaining comparable maximum colour densities.

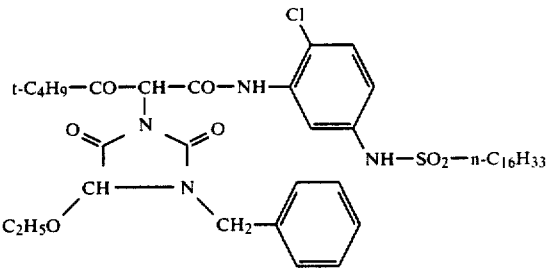

(Coupler 3 of DE-A 2 713 022)

EXAMPLE 6

Color photographic recording materials 16 to 19 were prepared as in Example 5, except that the emulsion described for layer 1 contained $5.10^{-2}$ mol of one of the yellow couplers 4, 5, D and E instead of the quantity of coupler mentioned there. Comparison coupler E was added in the form of a 5% aqueous alkaline solution.

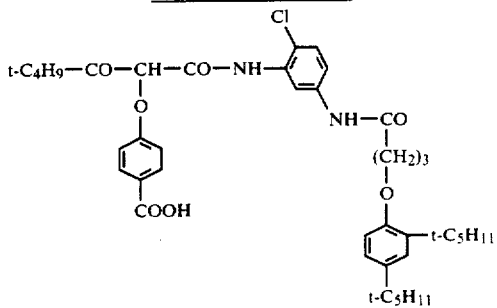

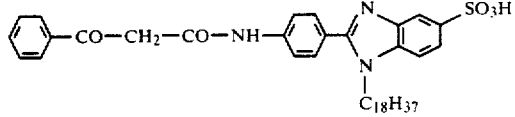

The procedure is otherwise the same as described in Example 5 but the reversal processing is modified in that the time for final washing is increased by the factor 3 in order to reduce as much as possible the quantity of residual chemicals from the processing baths and thus avoid secondary effects in the subsequent test for stability of the dyes. In the subsequent densitometric determination of the sample strips, that stage of the exposed wedge which had a density of almost 1 (=100%) was marked. A "speeded up stability test" was carried out by subsequently storing the material at 60° C. and 90% relative humidity over a period of 16 weeks. The density of the marked step was measured at intervals of two weeks and recorded in terms of the percentage of the original density. The result of the "speeded up stability test" is represented in FIG. 1. The ordinate shows the density of the marked step as a percentage of the original density (D≃1). The time is entered in weeks along the abscissa. The dyes obtained from the yellow couplers according to the invention are clearly more stable than those obtained from the comparison couplers.

We claim:

1. A color photographic recording material having at least one light-sensitive silver halide emulsion layer and a non-diffusible yellow coupler associated with this layer wherein the improvement comprises the yellow coupler corresponds to the following formula:

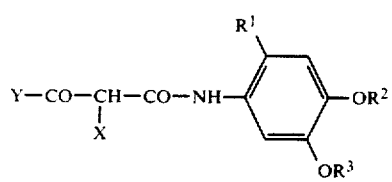

wherein

Y represents a p-alkoxyphenyl group selected from the group consisting of the following groups:

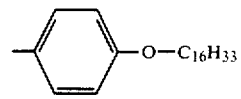

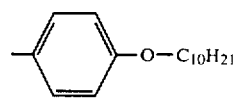

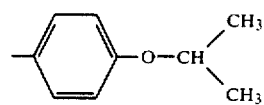

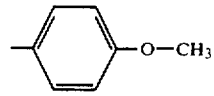

X represents a hydrogen atom or a group which is releasable in the process of color coupling, $R^1$ represents a halogen atom, and $R^2$ and $R^3$ represent identical or different alkyl groups, each having 1 to 20 carbon atoms, including substituted alkyl groups.

* * * * *